United States Patent
Laugharn, Jr. et al.

(10) Patent No.: US 9,080,167 B2
(45) Date of Patent: Jul. 14, 2015

(54) SYSTEM AND METHOD FOR PROCESSING PARAFFIN EMBEDDED SAMPLES

(71) Applicants: James A. Laugharn, Jr., Winchester, MA (US); Edwin Rudd, Salem, NH (US); Guillaume Durin, Boston, MA (US)

(72) Inventors: James A. Laugharn, Jr., Winchester, MA (US); Edwin Rudd, Salem, NH (US); Guillaume Durin, Boston, MA (US)

(73) Assignee: Covaris, Inc., Woburn, MA (US)

( * ) Notice: Subject to any disclaimer, the term of this patent is extended or adjusted under 35 U.S.C. 154(b) by 154 days.

(21) Appl. No.: 13/678,755

(22) Filed: Nov. 16, 2012

(65) Prior Publication Data

US 2014/0141413 A1 May 22, 2014

(51) Int. Cl.
*C12Q 1/68* (2006.01)
*C07H 21/00* (2006.01)
*C07K 1/00* (2006.01)
*C12N 15/10* (2006.01)

(52) U.S. Cl.
CPC .......... *C12N 15/1003* (2013.01); *C12Q 1/6806* (2013.01)

(58) Field of Classification Search
CPC ........ C12Q 1/68; C12Q 1/6806; C07H 21/00; C07H 21/04; C12N 15/1003; C07K 1/00
USPC .......... 435/6.1, 40.52; 530/412, 344; 422/128
See application file for complete search history.

(56) References Cited

U.S. PATENT DOCUMENTS

| | | | |
|---|---|---|---|
| 6,719,449 | B1 | 4/2004 | Laugharn |
| 6,948,843 | B2 | 9/2005 | Laugharn |
| 8,828,709 | B2 * | 9/2014 | Porschewski et al. ........ 435/272 |
| 2005/0130121 | A1 * | 6/2005 | Chong Conklin et al. ........ 435/4 |
| 2005/0233367 | A1 * | 10/2005 | Chu ................. 435/6 |
| 2008/0020380 | A1 * | 1/2008 | Patno et al. ........ 435/6 |
| 2012/0264228 | A1 * | 10/2012 | Poncelet et al. .......... 436/174 |
| 2014/0147348 | A1 * | 5/2014 | Katou et al. ............. 422/509 |

FOREIGN PATENT DOCUMENTS

WO    WO 2005116256 A2    12/2005

OTHER PUBLICATIONS

Banerjee et al. Microwave-based DNA extraction from paraffin-embedded tissue for PCR amplification. Biotechniques 18 (5) : 768 (1995).*
Bonin et al.,Multicentre validation study of nucleic acids extraction from FFPE tissues. Vischows Arch 457 : 309 (2010).*
Carolien et al. Expression Analysis on Archival Material: Comparison of 5 Commercially Available RNA Isolation Kits for FFPE Material. Diagnostic Molecular Pathology 18 (5) : 203 (Dec. 2011).*
Coombs et al. Optimisation of DNA and RNA extraction from archival formalin-fixed tissue. Nucleic Acids Research 27 (16) : e12 (1999).*
Farragher et al., RNA expression analysis from formalin fixed paraffin embedded tissues. Histochemistry and Cell Biology 130 : 435 (2008).*
Coombs, N. J. et al., Optimisation of DNA and RNA extraction from archival formalin-fixed tissue, Oxford University Press, GB, vol. 27, No. 16, Aug. 15, 1999, 3 pages.
Banerjee, S.K. et al., Microwave-based DNA extraction from paraffin-embedded tissue for PCR amplification, Biotechniques, Informa Healthcare, US, vol. 18, No. 5, Jan. 1, 1995, 4 pages.
Wu, S. et al., Microwave heating of long-term formalin-fixed surgical pathology specimens improves quality of extracted DNA, Applied Immunohistochemistry & Molecular Morphology: AIMM/Official Publication of the Society for Applied Immunohistochemistry, vol. 20, No. 5, Oct. 1, 2012, 6 pages.
International Search Report and Written Opinion dated Feb. 5, 2014 from corresponding PCT Application No. PCT/US2013/070290, p. 6.

* cited by examiner

*Primary Examiner* — Ethan C Whisenant
(74) *Attorney, Agent, or Firm* — Wolf, Greenfield & Sacks, P.C.

(57) ABSTRACT

Method and apparatus for processing paraffin embedded samples, e.g., to disassociate paraffin from tissue components and/or other biomolecules from the paraffin. The sample may be exposed to focused acoustic energy while held in a vessel containing a non-solvent, aqueous solution. Disassociated paraffin may be emulsified into the liquid or otherwise separated from the sample.

60 Claims, 2 Drawing Sheets

SYSTEM AND METHOD FOR PROCESSING PARAFFIN EMBEDDED SAMPLES

BACKGROUND

1. Field of the Invention

Systems and methods for processing of samples with acoustic energy are generally disclosed.

2. Related Art

Tissue samples, such as those taken by biopsy or other technique, are commonly formalin-fixed and paraffin embedded (FFPE) to allow for extended storage of the samples with relatively little degradation of DNA, RNA, proteins or other materials in the sample. In such FFPE processing, the samples are typically fixed in a formalin solution (e.g., a 10% formalin solution may contain 3.7% formaldehyde and 1.0 to 1.5% methanol), which creates crosslinks between nucleic acids, between proteins and/or between nucleic acids and proteins. Afterward, the sample is dehydrated, e.g., by placing the sample in an alcohol, and then "cleared" of the alcohol by exposing the sample to a solvent such as xylene. The sample is then embedded in paraffin, where the sample is surrounded by paraffin which replaces the xylene in the sample. The paraffin embedded sample can then be stored for extended periods of days, months, years.

To recover nucleic acid material (e.g., DNA and/or RNA) and/or proteomic material (e.g., proteins) from an FFPE sample, the paraffin must be disassociated from the sample. This is typically done by placing the paraffin-bearing sample in an organic solvent, such as xylene, heptane or limonene, to dissolve the paraffin or by heating the sample in mineral oil or aqueous buffer.

SUMMARY OF INVENTION

The inventors have found that exposing the sample to a solvent during paraffin removal tends to cause damage to the nucleic acid and/or proteome material or otherwise tends to reduce the yield of good quality nucleic acid and/or proteomic material recovered from an FFPE sample. In addition, the sample is now a hazardous organic solvent waste and proper disposal is more problematic. In accordance with one aspect of the invention, paraffin may be disassociated from an FFPE sample using a non-solvent solution, e.g., without exposing the sample to a solvent during the process of paraffin disassociation. Instead, a non-solvent solution, e.g., one that includes water and a detergent, may be used together with suitable focused acoustic energy to disassociate paraffin from a sample. Such paraffin removal may be done without exposing the sample to relatively high temperatures, e.g., paraffin may be suitably disassociated from the sample while maintaining the sample temperature below 40-60 degrees C. This paraffin removal technique has been found to increase nucleic acid material yield by 2 to 3 times that found with typical processes. In some embodiments, paraffin may be disassociated from a sample relatively quickly, e.g., in 3 minutes or less. Also, in some embodiments the sample may be rehydrated during the paraffin removal process, which has been found to improve bio-material yield as well.

In another aspect of the invention, a process for digesting crosslink materials in preparation for nucleic acid material purification is enhanced. In one embodiment, a FFPE sample may be exposed to a proteinase K enzyme or other protease along with suitable focused acoustic energy for a relatively short period, e.g., 30 seconds or less, to help enhance release of nucleic acid material by digesting crosslinks caused by the FFPE process. In some embodiments, the protease may be combined with a glycerol to enhance enzyme activity during acoustic treatment.

In one aspect of the invention, a method for processing a paraffin-embedded sample includes providing a paraffin-embedded tissue sample in a vessel, where the sample has previously been formalin fixed and embedded in paraffin and has paraffin attached to the sample. A non-solvent, aqueous solution is provided in the vessel with the paraffin-embedded sample, and paraffin is disassociated from the paraffin-embedded sample by exposing the sample and non-solvent solution in the vessel to acoustic energy to disassociate paraffin from the sample. Biomolecules, such as nucleic acids, proteins and/or other components, may be recovered from the aqueous portion of the sample after disassociation of paraffin, e.g., by pipetting liquid containing the biomolecules from the vessel.

The disassociation process may include exposing the sample to focused acoustic energy for a time sufficient to disassociate enough paraffin from the sample to allow recovery of nucleic and/or proteome material from the sample. For example, 90%, 95%, 98% or more of the paraffin initially attached to the sample may be disassociated from the sample, e.g., by emulsifying the paraffin. Since the liquid in the vessel is aqueous, disassociation of the paraffin may also include rehydrating the sample while exposing the sample to focused acoustic energy. Disassociation may performed while the vessel is located in a bath of liquid at a temperature of about 30-60 degrees C., e.g., the bath may be at a temperature of about 40 degrees C. Thus, disassociation may be performed while the a temperature of the sample is maintained below about 60 degrees C., e.g., below about 45 degrees C.

Recovery of the biomolecules may include a variety of different processes, such as adding a protease to the non-solvent aqueous solution and the sample in the vessel after removal of paraffin from the sample. The processed sample and a protease-containing solution may be exposed to focused acoustic energy a second time, e.g., for a period of 10-30 seconds (or more) to enhance the mixing of the protease with the sample and thereby enhance enzymatic activity. The mixed sample is then incubated with the protease to digest the tissue for 1 hour at an appropriate temperature. Crosslinks in the sample material may be reversed by an additional incubation at 80-90 degrees C. for an extended period, e.g., for 1 hour or more. The sample may also be exposed to focused acoustic energy suitable to shear nucleic acid material released from the sample into smaller fragments. For example, a majority of the fragments of nucleic acid material after exposing the sample to focused acoustic energy may have a size of 50 to 1000 bp. Protease treatment and/or nucleic acid fragmentation may be done in the vessel containing the disassociated paraffin and the sample as part of the recovering step.

In another aspect of the invention, an acoustic treatment device includes a vessel holding a formalin fixed, paraffin embedded tissue sample and a non-solvent, aqueous solution, and an acoustic energy source for providing acoustic energy to the sample while the sample is in the vessel and separated from the acoustic energy source. A vessel holder may support the vessel at a location at least partially in a focal zone of the acoustic energy, and a system control circuit may control the acoustic energy source to expose the sample to focused acoustic energy suitable to disassociate paraffin from the sample to allow recovery of biomolecules of the sample. In some embodiments, the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel. In addition, by combining paraffin disassociation, tissue sample rehydration, enzyme mixing, and tissue sample digestion into one vessel the process may be readily automated. For example, if the vessel includes a cap with a split septa, a protease may be added following the disassociation of the paraffin without removal of the cap.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
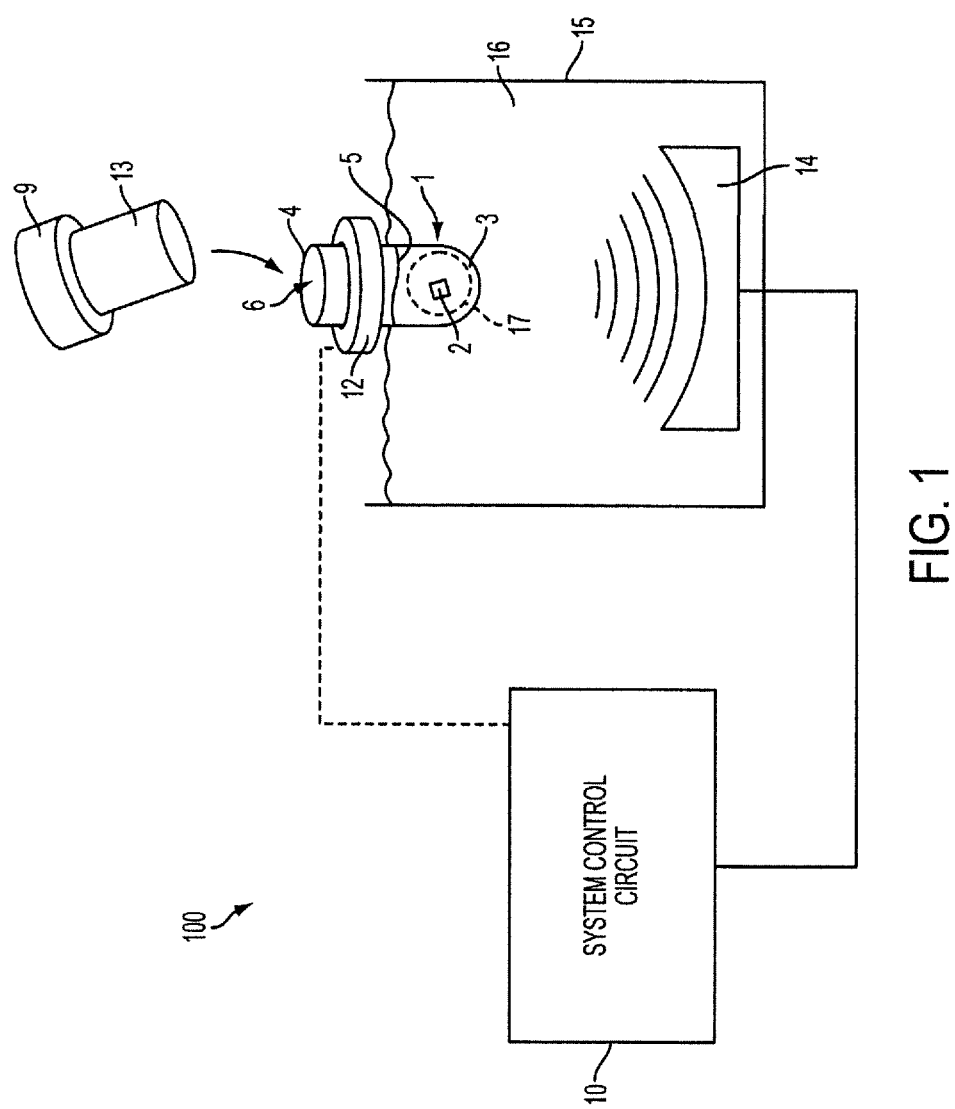
FIG. 1 shows a schematic block diagram of an acoustic treatment system that incorporates one or more aspects of the invention.

Aspects of the invention are not limited in application to the details of construction and the arrangement of components set forth in the following description or illustrated in the drawings. Other embodiments may be employed and aspects of the invention may be practiced or be carried out in various ways. Also, aspects of the invention may be used alone or in any suitable combination with each other. Thus, the phraseology and terminology used herein is for the purpose of description and should not be regarded as limiting.

As described above, chemical, biochemical, and acoustic treatment processes can be useful for disassociating paraffin from FFPE samples and/or digesting cross-linked proteins in the sample material with the end goal of recovering target molecules from the sample material, such as DNA, RNA, proteins, and the like. In addition, such systems may be used along with aspects of the invention for DNA/RNA shearing, e.g., to reduce the base pair length of DNA fragments from 1,000s or 10,000s of base pairs to lengths of 3 k base pairs or smaller. Examples of such acoustic treatment systems and control arrangements are described in U.S. Pat. Nos. 6,948, 843 and 6,719,449, assigned to Covaris of Woburn, Mass.

In some embodiments, aspects of the invention may allow for paraffin removal from a FFPE sample, protease treatment or other processing to digest unwanted material to release DNA/RNA from the sample, and/or shearing to fragment nucleic acid material into a desired size range all in a single vessel using a non-solvent aqueous solution and without the use of solvents. This series of steps performed in a single vessel and without the use of solvents is simply not possible with conventional techniques, and allows for improved nucleic acid material yield and decreased possibility for sample contamination.

In another aspect of the invention, an efficiency of use of acoustic energy in disassociating paraffin from the sample, enhancing activity of an enzyme and/or fragmentation of nucleic acid material may be enhanced, e.g., by reducing an amount of gas that is entrained in the sample and/or available for entrainment. In some embodiments, gas entrainment in a sample may be reduced by reducing or otherwise controlling a size of the headspace adjacent the sample. By reducing the volume and/or surface area of a headspace presented to a sample, an amount of gas available for entrainment into the sample can be reduced, or a rate at which the gas can be entrained may be reduced. This can help reduce bubble formation in the sample during acoustic treatment and/or interference of gas with cavitation bubble collapse, helping to increase an amount of acoustic energy that is used for treating the sample rather than being reflected out of the sample vessel or absorbed by increased cavitation bubble pressure.

FIG. 1 shows a schematic block diagram of an acoustic treatment system 100 that incorporates or is used with one or more aspects of the invention. It should be understood that although embodiments described herein may include most or all aspects of the invention, aspects of the invention may be used alone or in any suitable combination with other aspects of the invention. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1, e.g., the focal zone 17 may fit entirely within the vessel 4. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. In this embodiment, the vessel 4 is a 6×16 mm glass or plastic tube (approximately 150 microliter volume) having a screw cap, but it should be understood that the vessel 4 may have any suitable shape, size, material, or other feature. For example, the vessel 4 may be a cylindrical tube with a flat bottom and a threaded top end to receive a cap 9, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silica material), which is also attached to a vessel holder 12, which may be formed, at least in part, by an opening or other feature of the medium 16. Thus, the transducer 14, medium 16 and holder 12 may be formed as a single integrated part, if desired. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. In addition, or alternately, the transducer 14 may form the focal zone 17 so that the focal zone 17 is suitably positioned relative to the sample 1 or vessel 4.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

In this illustrative embodiment, the sample 1 includes a solid material 2, such as a tissue sample that has been formalin fixed and paraffin embedded (i.e., an FFPE sample) that is contained in the vessel 4 along with a liquid 3, e.g., a non-solvent aqueous solution. The non-solvent solution 3 may include water along with a detergent, e.g., a 0.25% SDS (sodium dodecyl sulfate) solution, although other solutions are possible. The sample may have any suitable volume and/or mass, e.g., the sample may be a so-called "scroll" or piece of FFPE tissue microtome sliced from a larger sample piece, a tissue sample taken by needle biopsy, or other. In some embodiments, a sample cut by microtome may have a thickness of about 7 to 25 micrometers and a length of 20 mm or less. For example, a sample may be sized to have a volume of about 4 cubic millimeters or less. Of course, depending on the application or sample involved, other volumes may be used, such as less than 10 cubic millimeters, less than 20 cubic millimeters, less than 50 cubic millimeters, less than 100 cubic millimeters, or less than 500 cubic millimeters.

In accordance with an aspect of the invention, care may be taken to suitably define a headspace 6 in the vessel 4 prior to acoustic treatment. That is, an interface 5 (or upper level of the liquid 3 in the vessel 4) may be separated from the cap 9 by a headspace 6, which is shown to be a gaseous region immediately above the interface 5. By appropriately setting the headspace 6 volume, efficiency of the paraffin disassociation, protease treatment and/or nucleic acid fragmentation process may be enhanced. For example, some acoustic energy power levels at the focal zone 17 suitable to cause mixing, e.g., lysing, extraction, permeabilizing, catalyzing, degrading, fluidization, heating, particle breakdown, shearing and/or disruption of molecular bonds in the sample 1, may also cause portions of the sample 1 (including solid material 2 and/or liquid material 3) to be splashed or otherwise ejected from the interface 5. In some cases, the ejected sample 1 may return to the main volume of sample 1, but in other cases, the ejected sample 1 may adhere to the vessel 4 above the interface 5 or otherwise fail to return to the main sample 1. In either case, the ejected sample 1 may spend a reduced amount of time in the focal zone 17.

In addition, or alternately, acoustic energy may cause gas in the headspace 6 to be entrained into the liquid 3, such as by dissolving a portion of the gas in the headspace 6 and/or by capturing bubbles of headspace gas in the sample due to motion of the liquid at the interface 5. Gas in the liquid 3 may interfere with acoustic energy, such as by gas bubbles at or near the focal zone 17 reflecting acoustic energy away from the sample 1 and/or by dissolved gas increasing a pressure in cavitation bubbles created by acoustic energy, thereby decreasing the rate or force at which the cavitation bubbles collapse. It is believed that the collapse of cavitation bubbles transfers significant kinetic energy to sample materials, causing the materials to be lysed, sheared or otherwise mechanically operated on. By increasing a pressure in such bubbles, dissolved gas in the sample can reduce the energy released by cavitation bubble collapse, reducing an effectiveness of acoustic treatment. Thus, by controlling headspace size (volume and/or surface area presented at the interface 5), efficiency of the acoustic treatment processing can be improved. In this illustrative embodiment, liquid 3 may be provided in the vessel so that the interface 5 is within about 1-2 mm of the cap 9. However, other headspace sizes are possible, including a headspace that is 20% of the liquid 3 volume, 10% of the liquid volume, 5% of the liquid volume, or 0% of the liquid volume. As shown in FIG. 1, the cap 9 may have a headspace control member 13, such as a lower portion of the cap 9 that is controllably positionable relative to the interface 5, or the headspace 6 may be controlled by suitably filling the vessel 4. The cap 9 may also include a metal or ceramic component (e.g., a disc about 1 mm thick) or other relatively hard surface positioned adjacent the interface 5 to help reflect acoustic energy back toward the sample 1. This may help enhance efficiency of acoustic processing.

With the sample 1 and liquid 3 in the vessel 4, the vessel 4 may be associated with a holder 12 that helps support the vessel 4 during acoustic treatment. The holder 12 may take any suitable arrangement, such as a ring-shaped element 12 that is fixed relative to the vessel 4, as shown in FIG. 1. Although in the FIG. 1 embodiment the holder 12 is located near a middle of the vessel 4, the holder 12 may be positioned in any suitable manner relative to the vessel 4, such as near the bottom or top of the vessel, extending from one side of the vessel, and/or any other appropriate position. The holder 12 may be permanently fixed to the vessel 4, e.g., molded integrally with the vessel 4, attached to the vessel 4 by an adhesive, a fastener, welding, etc., or may be removably attached to the vessel. For example, in some embodiments, the vessel holder 12 may include a ring member like that shown in FIG. 1 and one or more O-rings (not shown) or other friction-enhancing elements that are positioned between the ring member and the vessel 4 to provide a tight friction fit between the vessel 4 and the holder 12. Such an arrangement may be useful when interchanging vessels 4 on a single holder 12 and/or adjusting the position of the vessel 4 relative to the holder 12.

Although a vessel holder 12 is not necessarily required, the vessel holder 12 may serve to interface with the acoustic processing device so that the vessel 4 and the sample in the vessel is positioned in a known location relative to an acoustic field, for example, at least partially within a focal zone 17 of acoustic energy. Also, the holder 12 is not limited to a device like that shown in FIG. 1, and instead may include a rack, slot, tray, gripper element, clamp, box or any other suitable arrangement for holding and/or moving the vessel 4 with respect to the focal zone 17.

With the vessel 4 and sample 1 suitably positioned relative to the acoustic transducer 14, acoustic treatment of the sample 1 may be performed to disassociate paraffin from the sample 1. During this process the coupling medium 16 may be maintained at a relatively low temperature, e.g., 40-60 degrees C., although lower or higher temperatures are possible. Thus, the sample 1 may be maintained at a relatively low temperature during paraffin disassociation, e.g., the sample 1 may not exceed a temperature of 40-60 degrees C. during processing, and in some cases may remain below a melting temperature of the paraffin. As a result, paraffin may be disassociated from sample material without causing bulk melting of the paraffin. In an embodiment where the acoustic treatment system 100 is a Covaris S220 or E220 model, acoustic treatment may be applied using a 10% duty cycle, a peak incident power of 175 watts, 200 cycles per burst for about 150 seconds. Of course, other duty cycles, peak power, cycles per burst and/or time periods may be used. The coupling medium 16, which may be water, may be kept at a temperature of 46 degrees C. during the paraffin disassociation processing. Also, since the liquid is a non-solvent, aqueous solution, the sample 1 may be rehydrated during paraffin disassociation. While exposing the sample to focused acoustic energy during the disassociation process, the liquid 3 will tend to appear opalescent as the paraffin is emulsified or otherwise separated from tissue portions of the sample.

Upon completion of the paraffin disassociation process, biomolecules or other portions of the tissue sample may be recovered from the vessel, e.g., by centrifuging and/or pipetting the sample portions from the vessel, and the recovered sample portions may be subsequently treated in another vessel or holder, e.g., to recover nucleic acid, protein or other components of the sample. In one aspect of the invention, further processing of the sample, such as protease digestion, nucleic acid fragmentation, centrifugation and/or other processes may be performed in the same vessel. Performing multiple processes, e.g., as part of nucleic acid purification protocol, in a single vessel may not only simplify the overall process, but also reduces transfer losses and the chance that the sample is contaminated in some way.

In one illustrative embodiment, after paraffin disassociation is complete, a protease, such as proteinase K or trypsin, may be added to the vessel with or without removal of the disassociated paraffin from the vessel. As is known to those of skill in the art, a protease may function to digest proteins as a precursor to recovering desired nucleic acids, protein fragments or other biomolecules. In accordance with an aspect of the invention, the vessel containing a protease may be treated with acoustic energy to enhance mixing and/or activity of the protease. In one embodiment, acoustic treatment for 30 seconds or less (e.g., 10 seconds) may serve to suitably mix the protease with the sample prior to incubating the sample with the protease to further hydrolyize the proteins in the sample. Also, the inclusion of a glycerol material with the protease is thought to further enhance the enzyme activity and the effect of the acoustic energy as a driver of the protease action. This mixing treatment may be performed with the sample at a temperature of between 40-46 degrees C., e.g., with the coupling medium 16 at about 46 degrees C., although other temperatures are possible.

After protein digestion, the sample may be incubated with the protease at 80-90 degrees C. to reverse formaldehyde cross links, e.g., at about 80 degrees C. This incubation may be performed with or without acoustic treatment of any kind. After incubation, nucleic acids, proteins or other biomolecules may be recovered from the vessel, e.g., by centrifuging and pipetting the processed suspension from the vessel. The recovered biomolecules may be subjected to any suitable further processing as desired, such as DNA purification processing using commercially available techniques and equipment. In some embodiments, the sample may be subjected to a third acoustic treatment to fragment nucleic acids in the sample into a desired size range. For example, the starting DNA material after protease incubation and revser crosslink may include DNA segments having a size of about 7-50 kbp or more. Acoustic treatment may be provided, e.g., using a Covaris S2 AFA machine employing a 10% duty factor, 175 watts peak intensity power, and 200 cycles per burst for approximately 7-8 minutes, to shear the DNA material. After treatment, a majority (if not all) of the DNA fragments in the sample 1 may be reduced in size to about 200 bp. That is, a fairly narrow range of final DNA fragment sizes may be produced, e.g., most of the DNA fragments may fall in a size range of about 50 bp to about 500 bp, and the range of DNA fragment sizes produced may be adjusted by adjusting characteristics of the acoustic treatment.

Figure 2:
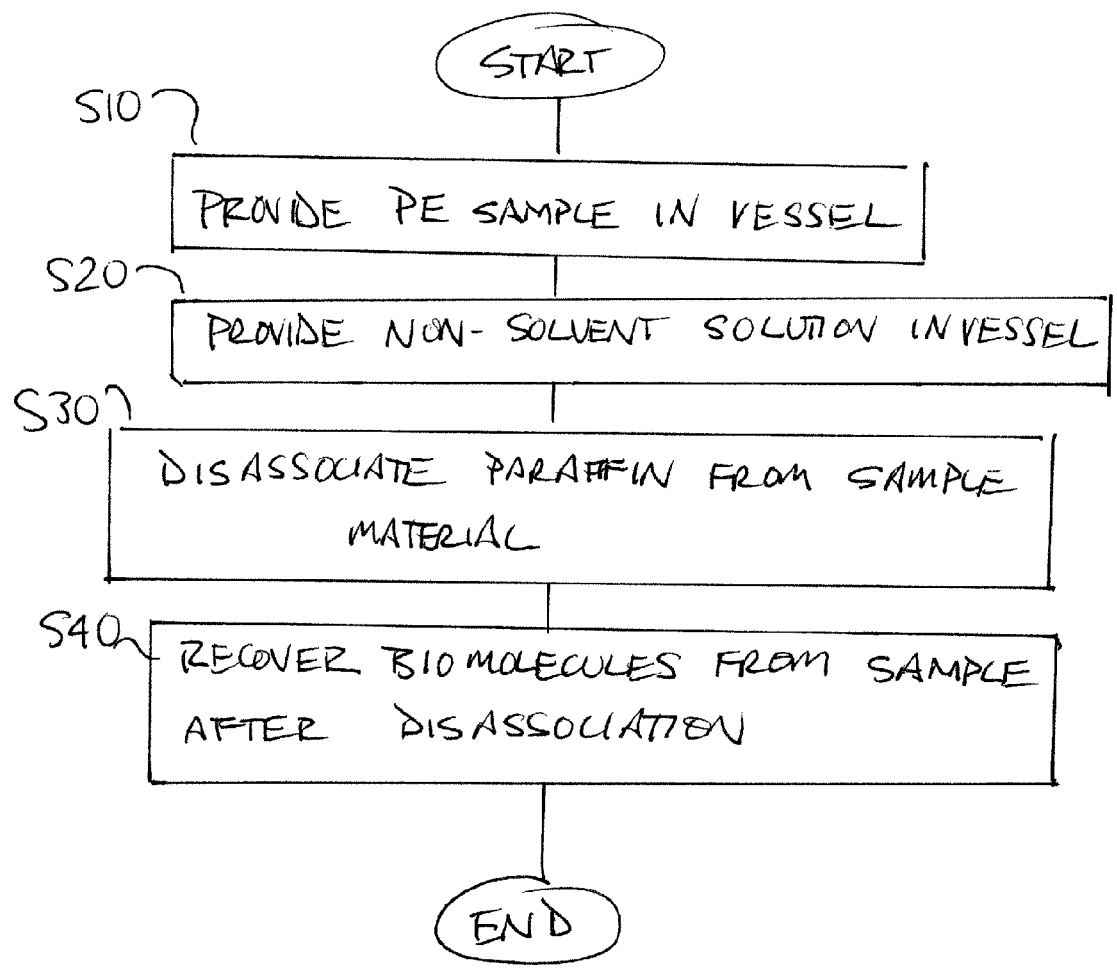
FIG. 2 shows steps in a method for processing a paraffin embedded sample.

FIG. 2 shows a flow chart of steps in a method for processing a paraffin-embedded sample, such as a formalin fixed, paraffin embedded sample. In step S10, a paraffin-embedded sample is provided in a vessel. While in this embodiment, the sample is a FFPE sample, the sample need not necessarily be formalin fixed, but instead may simply be paraffin embedded, e.g., the sample may be encased in a bolus of paraffin or otherwise have paraffin attached to the sample. The sample may be any suitable type of sample, such as animal or plant tissue, whether muscle, connective tissue, bone, a seed, etc. The sample may be harvested in any suitable way, such as by surgical techniques, a biopsy needle, etc., and all or a portion of the sample may be provided in the vessel. For example, a tissue sample may be embedded in paraffin and a slice or other piece of the sample may be cut by microtome or other technique from a larger piece and placed in a vessel. In some embodiments, excess paraffin may be removed from the sample prior to placement in the vessel, e.g., excess paraffin portions may be cut or broken off prior to placement of the sample in the vessel. The sample may have any suitable size and/or shape, e.g., may be a "scroll" or relatively thin, flat piece of tissue (which may be curled or rolled, or not), and may have any suitable volume. In one illustrative embodiment, a "scroll" may have a thickness of about 5 to 25 microns, and a width and length of about 10-30 mm. Of course, the sample may be arranged in other ways and have other suitable shapes, such as cylindrical, spherical, irregular, multiple separate parts, etc.

The vessel may have any suitable arrangement, shape, volume, etc., so long as the vessel is arranged to hold the sample and permit acoustic treatment of the sample suitable to disassociate paraffin from the sample material. In some embodiments, the vessel may be a glass or plastic tube with a cap or cover, and have a volume of about 10-100 microliters or more. In one embodiment, the vessel is a 6×16 mm tube having a 150 microliter volume. The vessel may have a mechanism to allow control of a headspace in the vessel, e.g., a movable member may be arranged for positioning relative to an upper surface or interface of liquid in the vessel. Proper adjustment of the headspace volume and/or height may allow for more efficient acoustic processing of the sample, though is not necessarily required.

In step S20, a non-solvent liquid is provided in the vessel with the sample. The liquid may be aqueous, and may include a detergent material, such as SDS at a concentration of about 0.25% although other suitable concentrations or materials may be used. The liquid may be provided in sufficient volume (consistent with the selected volume of the vessel) to allow for proper emulsification of paraffin attached to the sample. Thus, the volume of liquid should be suitably large enough to allow for proper paraffin disassociation, and may be approximately 1 to 10 times or more the volume of the sample. Also, liquid may be provided to the vessel in an amount to control a headspace in the vessel as desired, e.g., to within about 1-2 mm of the vessel cap. For example, the liquid may be provided so that an interface of the liquid is suitably near a cap or other headspace control element of the vessel. Water provided with the liquid should preferably be distilled or otherwise suitably free of materials that might interfere with paraffin disassociation and/or subsequent processing, e.g., be molecular biology grade water. The sample and liquid may be provided at a suitable temperature, such as 40-60 degrees C.

In step S30, paraffin is disassociated from the sample by exposing the sample and liquid in the vessel to suitable acoustic energy. In one embodiment, the sample is exposed to focused acoustic energy sufficient to homogenize the sample and disassociate the paraffin from the sample. The sample may be exposed to focused acoustic energy for a time sufficient to disassociate enough paraffin from the sample to allow recovery of nucleic acid and/or proteome material from the sample, e.g., acoustic energy may be applied to the sample for about 100-200 seconds in some embodiments, such as 150 seconds. In some embodiments, the acoustic energy has a frequency of between about 100 kilohertz and about 100 megahertz and has a focal zone with a width of less than about 2 centimeters. The acoustic energy may originate from an acoustic energy source spaced from and exterior to the vessel, e.g., the acoustic energy may pass through a coupling medium to the vessel, such that at least a portion of the acoustic energy propagates exterior to the vessel. A peak incident power level of the acoustic energy may be about 175 watts, although other power levels, such as between 100 and 400 watts, may be used.

During this process, 90%, 95%, 98% or more of the paraffin attached to the sample may be disassociated and caused to be emulsified or otherwise dispersed into the liquid. In some embodiments, disassociation of the paraffin may occur at temperatures below the melting temperature of the paraffin, e.g., the vessel may be located in a bath of liquid (such as a water-based acoustic coupling medium) at a temperature of about 30-50 degrees C., such as about 40 or 46 degrees C. Thus, in some examples, the paraffin may be disassociated from the sample while the sample remains below a temperature of about 55 degrees C.

In step S40, biomolecules of the sample may be recovered from the vessel that are essentially free of paraffin. This recovery may be performed in any suitable way, such as by physically grasping material in the vessel and removing the material, pipetting liquid and sample material from the vessel, filtering the sample material from the liquid, centrifuging the vessel to separate sample material from paraffin and/or other material in the vessel, and so on. Additional processes may be involved in the recovery of biomolecules from the sample, including digesting proteins or other substances in the sample, shearing or fragmenting nucleic acids, additional acoustic treatment after paraffin disassociation, adding reagents or other substances to the vessel, and so on.

For example, a protease may be added to the non-solvent aqueous solution and the sample in the vessel after disassociation of paraffin from the sample. In some embodiments, the protease, which may be proteinase K or trypsin, may be added to the vessel without removing the disassociated paraffin. Also, or alternately, after addition of the proteinase K or trypsin, the sample may be again exposed to acoustic energy, e.g., focused acoustic energy, arranged to mix the sample and protease, and thereby enhance activity of the proteinase K or trypsin. For example, the sample and proteinase K or trypsin may be exposed to 10-30 seconds (or more) of focused acoustic energy to mix the protease and sample. After acoustic treatment, an incubation of the sample with the proteinase K or trypsin such as at about 56 degrees C. for proteinase K, an additional incubation of the sample may be done for an extended period, e.g., for 1 hour or more, at a suitable temperature, such as about 80 or 90 degrees C. to reverse crosslinks in the sample material.

If nucleic acids in the sample are to be fragmented and recovered from the sample, the sample (e.g., in the same vessel and liquid used in paraffin disassociation and/or protease digestion, or in another vessel) may be subjected to acoustic processing to shear DNA or RNA fragments into a desired size range. For example, after exposing the sample to focused acoustic energy, nucleic acid material may be fragmented such that a majority of the fragments have a size of 50 to 500 bp. Thereafter, the fragmented nucleic acids may be recovered, e.g., by centrifuging the vessel (or its contents) and pipetting the nucleic acids from the vessel, leaving the paraffin (if present) and/or other materials in the vessel. The recovered nucleic acids present in the aqueous phase of the sample may be then purified or otherwise processed, e.g., using known techniques for purification. For example, the sample may be added to a chaotropic salt solution, usually containing guanidine, and ethanol may be added to the nucleic acid material and mixed by vortexing. The volumes of salt solution and ethanol used will typically be scaled to the liquid volume of the sample. After mixing by vortexing, the vessel may be centrifuged (e.g., at 10,000×g for 2 minutes) at room temperature or other suitable temperature. After centrifugation, paraffin particles, if present in the vessel, will form a white, floating layer on top of the liquid. The vessel may be held at the same angle as in the centrifuge rotor, and a pipet used to recover the nucleic acid-containing liquid from the vessel. The liquid may then be transferred to a silica membrane column. Generally, any transfer of some paraffin particles from the vessel is acceptable and will not interfere with the nucleic acid purification.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

Example

A comparison test was performed to compare nucleic acid (DNA in this case) yield from an FFPE sample using processes in accordance with aspects of the invention with the yield obtained using a Promega ReliaPrep FFPE gDNA Miniprep system. A buffer containing 0.25% of SDS was used to disassociate paraffin from the sample. 106 microliters of this buffer was loaded into a Covaris microTUBE Screw-Cap vessel. Two pieces of scroll, 20 micrometers in thickness and a weight of less than 5 mg were loaded in the same microTUBE vessel. A first acoustic treatment (with a Covaris E or S-Series) consisting of 175 W, 10% duty factor, 150 seconds and 200 cycles per burst at 41 degrees C. was used to disassociate the paraffin from the sample and rehydrate it. 20 microliters of Proteinase K (at 20 mg/ml) was then added in the same microTUBE vessel. A short acoustic treatment (175 W/10% duty factor/10 seconds/200 cycles per burst) was then done to mix the Proteinase K and the sample. The sample was then incubated at 56 degrees C. for an hour to let the Proteinase K digest the tissue. Another incubation step of an hour at 80 degrees C. was then realized to reverse the crosslink between nucleic acids and proteins. At the end, using the same microTUBE vessel and without transferring the sample or paraffin, an acoustic treatment (175 W/10% duty factor/200 cycles per burst/430 seconds) was done to fragment the DNA to a size suitable for next gen sequencing. The acoustic treatment reduced the fragment size to a distribution centered on 200 bp and comprised between 50 and 500 bp. In short, when the DNA fragments were purified and quantitated from the above example, the yield was 2 to 3 times the yield obtained with the Promega system.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method for processing a paraffin-embedded sample, comprising:
   providing a paraffin-embedded tissue sample in a vessel, the sample having previously been formalin fixed and embedded in paraffin;
   providing a non-solvent solution in the vessel with the paraffin-embedded sample;
   disassociating paraffin from the paraffin-embedded sample by exposing the sample and non-solvent solution in the vessel to acoustic energy to disassociate paraffin from the sample, wherein the step of disassociating comprises exposing the sample to focused acoustic energy while the vessel is located in a bath of liquid at a temperature of about 30-60 degrees C.; and
   recovering biomolecules from the sample after disassociation of paraffin from the sample.

2. The method of claim 1, wherein the step of disassociating comprises exposing the sample to focused acoustic energy for a time sufficient to disassociate enough paraffin from the sample to allow recovery of nucleic and/or proteomic material from the sample.

3. The method of claim 1, wherein the step of disassociating comprises disassociating more than 90% of paraffin attached to the sample.

4. The method of claim 1, wherein the step of disassociating comprises disassociating more than 98% of paraffin attached to the sample.

5. The method of claim 1, wherein the step of disassociating comprises rehydrating the sample while exposing the sample to focused acoustic energy.

6. The method of claim 1, wherein the bath is at a temperature of about 40 degrees C.

7. The method of claim 1, wherein the step of disassociating comprises maintaining a temperature of the sample below about 60 degrees C.

8. The method of claim 1, wherein the sample has a thickness of 5 to 25 microns and a length of less than 25 mm.

9. The method of claim 1, further comprising adding a protease to the non-solvent solution and the sample in the vessel after disassociation of paraffin from the sample.

10. The method of claim 9, further comprising exposing the sample, the protease and the non-solvent solution to focused acoustic energy to mix the sample, the protease and the non-solvent solution together.

11. The method of claim 10, wherein the step of exposing the sample, the protease and the non-solvent solution to focused acoustic energy comprises exposing the sample to focused acoustic energy suitable to fragment nucleic acid material from the sample into smaller fragments.

12. The method of claim 11, wherein a majority of the fragments of nucleic acid material after exposing the sample to focused acoustic energy to fragment nucleic acid material have a size of 50 to 1000 bp.

13. The method of claim 11, wherein the vessel contains the paraffin disassociated from the sample during the recovering step.

14. The method of claim 12, wherein the step of recovering includes pipetting the sample, disassociated paraffin and non-solvent solution of nucleic acid and/or proteome material from the vessel.

15. The method of claim 9, further comprising incubating the sample in the vessel with the protease and the non-solvent solution at a temperature to reverse formaldehyde crosslinks in the sample.

16. The method of claim 9, further comprising incubating the sample in the vessel with the protease and the non-solvent solution at a temperature of 50-60 degrees C. to digest the tissue in the sample.

17. The method of claim 1, wherein the recovering step includes centrifuging the vessel containing the sample, disassociated paraffin and non-solvent solution of nucleic acid and/or proteome material to transfer the contents from the vessel to a second container.

18. The method of claim 17, further comprising purifying nucleic acid material recovered from the vessel.

19. The method of claim 1, wherein the acoustic energy has a frequency of between about 100 kilohertz and about 100 megahertz and has a focal zone with a width of less than about 2 centimeters, and the acoustic energy originates from an acoustic energy source spaced from and exterior to the vessel, wherein at least a portion of the acoustic energy propagates exterior to the vessel.

20. The method of claim 1, wherein the step of providing a non-solvent solution includes defining a headspace in the vessel such that an upper level of the solution is within 2 mm of a cap placed on the vessel.

21. A method for processing a paraffin-embedded sample, comprising:
providing a paraffin-embedded tissue sample in a vessel, the sample having previously been formalin fixed and embedded in paraffin;
providing a non-solvent solution in the vessel with the paraffin-embedded sample;
disassociating paraffin from the paraffin-embedded sample by exposing the sample and non-solvent solution in the vessel to acoustic energy to disassociate paraffin from the sample, wherein the step of disassociating comprises maintaining a temperature of the sample below about 60 degrees C.; and
recovering biomolecules from the sample after disassociation of paraffin from the sample.

22. The method of claim 21, wherein the step of disassociating comprises exposing the sample to focused acoustic energy for a time sufficient to disassociate enough paraffin from the sample to allow recovery of nucleic and/or proteomic material from the sample.

23. The method of claim 21, wherein the step of disassociating comprises disassociating more than 90% of paraffin attached to the sample.

24. The method of claim 21, wherein the step of disassociating comprises disassociating more than 98% of paraffin attached to the sample.

25. The method of claim 21, wherein the step of disassociating comprises rehydrating the sample while exposing the sample to focused acoustic energy.

26. The method of claim 21, wherein the step of disassociating comprises exposing the sample to focused acoustic energy while the vessel is located in a bath of liquid at a temperature of about 30-60 degrees C.

27. The method of claim 26, wherein the bath is at a temperature of about 40 degrees C.

28. The method of claim 21, wherein the sample has a thickness of 5 to 25 microns and a length of less than 25 mm.

29. The method of claim 21, further comprising adding a protease to the non-solvent solution and the sample in the vessel after disassociation of paraffin from the sample.

30. The method of claim 29, further comprising exposing the sample, the protease and the non-solvent solution to focused acoustic energy to mix the sample, the protease and the non-solvent solution together.

31. The method of claim 30, wherein the step of exposing the sample, the protease and the non-solvent solution to focused acoustic energy comprises exposing the sample to focused acoustic energy suitable to fragment nucleic acid material from the sample into smaller fragments.

32. The method of claim 31, wherein a majority of the fragments of nucleic acid material after exposing the sample to focused acoustic energy to fragment nucleic acid material have a size of 50 to 1000 bp.

33. The method of claim 31, wherein the vessel contains the paraffin disassociated from the sample during the recovering step.

34. The method of claim 32, wherein the step of recovering includes pipetting the sample, disassociated paraffin and non-solvent solution of nucleic acid and/or proteome material from the vessel.

35. The method of claim 29, further comprising incubating the sample in the vessel with the protease and the non-solvent solution at a temperature to reverse formaldehyde crosslinks in the sample.

36. The method of claim 29, further comprising incubating the sample in the vessel with the protease and the non-solvent solution at a temperature of 50-60 degrees C. to digest the tissue in the sample.

37. The method of claim 21, wherein the recovering step includes centrifuging the vessel containing the sample, disassociated paraffin and non-solvent solution of nucleic acid and/or proteome material to transfer the contents from the vessel to a second container.

38. The method of claim 37, further comprising purifying nucleic acid material recovered from the vessel.

39. The method of claim 21, wherein the acoustic energy has a frequency of between about 100 kilohertz and about 100 megahertz and has a focal zone with a width of less than about 2 centimeters, and the acoustic energy originates from an acoustic energy source spaced from and exterior to the vessel, wherein at least a portion of the acoustic energy propagates exterior to the vessel.

40. The method of claim 21, wherein the step of providing a non-solvent solution includes defining a headspace in the vessel such that an upper level of the solution is within 2 mm of a cap placed on the vessel.

41. A method for processing a paraffin-embedded sample, comprising:
providing a paraffin-embedded tissue sample in a vessel, the sample having previously been formalin fixed and embedded in paraffin;
providing a non-solvent solution in the vessel with the paraffin-embedded sample;
disassociating paraffin from the paraffin-embedded sample by exposing the sample and non-solvent solution in the vessel to acoustic energy to disassociate paraffin from the sample, wherein the acoustic energy has a frequency of between about 100 kilohertz and about 100 megahertz and has a focal zone with a width of less than about 2 centimeters, and the acoustic energy originates from an acoustic energy source spaced from and exterior to the vessel, wherein at least a portion of the acoustic energy propagates exterior to the vessel; and
recovering biomolecules from the sample after disassociation of paraffin from the sample.

42. The method of claim 41, wherein the step of disassociating comprises exposing the sample to focused acoustic energy for a time sufficient to disassociate enough paraffin from the sample to allow recovery of nucleic and/or proteomic material from the sample.

43. The method of claim 41, wherein the step of disassociating comprises disassociating more than 90% of paraffin attached to the sample.

44. The method of claim 41, wherein the step of disassociating comprises disassociating more than 98% of paraffin attached to the sample.

45. The method of claim 41, wherein the step of disassociating comprises rehydrating the sample while exposing the sample to focused acoustic energy.

46. The method of claim 41, wherein the step of disassociating comprises exposing the sample to focused acoustic energy while the vessel is located in a bath of liquid at a temperature of about 30-60 degrees C.

47. The method of claim 46, wherein the bath is at a temperature of about 40 degrees C.

48. The method of claim 41, wherein the step of disassociating comprises maintaining a temperature of the sample below about 60 degrees C.

49. The method of claim 41, wherein the sample has a thickness of 5 to 25 microns and a length of less than 25 mm.

50. The method of claim 41, further comprising adding a protease to the non-solvent solution and the sample in the vessel after disassociation of paraffin from the sample.

51. The method of claim 50, further comprising exposing the sample, the protease and the non-solvent solution to focused acoustic energy to mix the sample, the protease and the non-solvent together.

52. The method of claim 51, wherein the step of exposing the sample, the protease and the non-solvent solution to focused acoustic energy comprises exposing the sample to focused acoustic energy suitable to fragment nucleic acid material from the sample into smaller fragments.

53. The method of claim 52, wherein a majority of the fragments of nucleic acid material after exposing the sample to focused acoustic energy to fragment nucleic acid material have a size of 50 to 1000 bp.

54. The method of claim 52, wherein the vessel contains the paraffin disassociated from the sample during the recovering step.

55. The method of claim 53, wherein the step of recovering includes pipetting the sample, disassociated paraffin and non-solvent solution of nucleic acid and/or proteome material from the vessel.

56. The method of claim 50, further comprising incubating the sample in the vessel with the protease and the non-solvent solution at a temperature to reverse formaldehyde crosslinks in the sample.

57. The method of claim 50, further comprising incubating the sample in the vessel with the protease and the non-solvent solution at a temperature of 50-60 degrees C. to digest the tissue in the sample.

58. The method of claim 41, wherein the recovering step includes centrifuging the vessel containing the sample, disassociated paraffin and non-solvent solution of nucleic acid and/or proteome material to transfer the contents from the vessel to a second container.

59. The method of claim 58, further comprising purifying nucleic acid material recovered from the vessel.

60. The method of claim 41, wherein the step of providing a non-solvent solution includes defining a headspace in the vessel such that an upper level of the solution is within 2 mm of a cap placed on the vessel.

* * * * *